United States Patent [19]

Buckley et al.

[11] 4,187,375
[45] Feb. 5, 1980

[54] PROCESS FOR PREPARING OXAZINE RING COMPOUNDS

[75] Inventors: Thomas F. Buckley, Albany, Calif.; John G. Gleason, Delran, N.J.

[73] Assignee: SmithKline Corporation, Philadelphia, Pa.

[21] Appl. No.: 955,294

[22] Filed: Oct. 27, 1978

Related U.S. Application Data

[60] Division of Ser. No. 913,181, Jun. 6, 1978, Pat. No. 4,162,250, which is a division of Ser. No. 822,774, Aug. 8, 1977, Pat. No. 4,122,262, which is a continuation-in-part of Ser. No. 721,251, Sep. 8, 1976, Pat. No. 4,089,956.

[51] Int. Cl.² ........................................... C07D 265/04
[52] U.S. Cl. ................................................ 544/92
[58] Field of Search ................................... 544/92, 90

[56] References Cited

U.S. PATENT DOCUMENTS

| | | | |
|---|---|---|---|
| 4,011,216 | 3/1977 | Menard et al. | 544/90 |
| 4,013,648 | 3/1977 | Horning et al. | 544/90 |
| 4,013,653 | 3/1977 | Wolfe | 544/90 |
| 4,089,956 | 5/1978 | Buckley et al. | 544/92 X |

*Primary Examiner*—John D. Randolph
*Attorney, Agent, or Firm*—William H. Edgerton

[57] ABSTRACT

A new process for preparing oxazine ring compounds comprises cyclization of an azetidinone-1-hydroxyacetate in the presence of a proton source.

2 Claims, No Drawings

PROCESS FOR PREPARING OXAZINE RING COMPOUNDS

This application is a division of Ser. No. 913,181, filed June 6, 1978, now U.S. Pat. No. 4,162,250, which in turn was a division of Ser. No. 822,774, filed Aug. 8, 1977, now U.S. Pat. No. 4,122,262, which is a continuation-in-part of Ser. No. 721,251, filed Sept. 8, 1976, now U.S. Pat. No. 4,089,956.

This invention comprises a new series of bicyclic antibacterial agents as well as methods and intermediates for preparing them together with methods and compositions for using them as antibacterial agents. The compounds are characterized by having the 3-acylaminoazetidinone system of the known cephalosporin family of antibacterially active compounds but in place of the six membered dihydrothiazine ring of the cephalosporins there is present a six membered perhydro-1,3-oxazine ring. Representative are the 7-acylamino-4-loweralkoxy-8-oxo-3-oxa-1-azabicyclo[4.2.0]octane-2-carboxylic acid derivatives described hereafter.

These compounds are represented by the following structure:

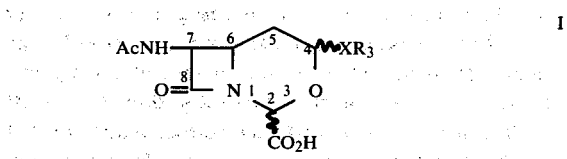

I in which:
Ac is any pharmaceutically acceptable acyl group present on the amino group at the 7-position of antibacterial cephalosporins or at the 6-position of antibacterial penicillins known to the art,
X is thio or preferably oxy, and
$R_3$ is a saturated or unsaturated, substituted or unsubstituted lower alkyl of from 1-4 carbon atoms.

Preferably $R_3$ is methyl or ethyl. Examples of substitution of the 4-alkoxy group may be halo such as chloro, bromo or fluoro, monophenyl, monohydroxy or monoacetoxy. The substitution or unsaturation of the 4-alkoxy substituent may be limited by the synthetic procedures as will be recognized by those skilled in the art from this disclosure but may vary over a wide range of substituents. The unsaturation may be for convenience of the allyl type.

It will be noted that in this general description of the invention the term alkoxy referring to the 4-substituent refers to the lower alkylthio as well.

Representative acyl substituents are:

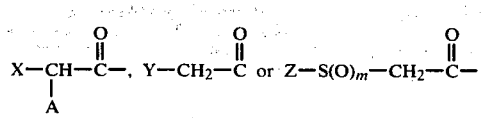

wherein:
X is thienyl, furyl, phenyl or phenyl monosubstituted with with hydroxy, hydroxymethyl, formamido or ureido;
A is $NH_2$, OH, COOH, $SO_3H$, formyloxy or, when the α-C-hydrogen is absent, methoxyimino;
Y is cyano, sydnone, pyridone, thienyl, phenoxy, phenyl, o-aminomethylphenyl or tetrazolyl;
Z is methyl, trifluoromethyl, trifluoroethyl, pyridyl or cyanomethyl; and
m is zero to two.

It will be recognized that the 2-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such esters are included within the scope of this invention. In the preparation of such esters strongly acid reaction conditions are to be avoided since the oxazine ring is susceptable to splitting under relatively strong acid reaction conditions. Of course the desired 7-acyl as well as a protective or functional ester or ether group can be inserted prior to the ring formation as noted in Scheme A below.

A group of compounds of this invention is represented by Formula I where $R_3$ is methyl and X is oxy.

Another subgeneric group of compounds of this invention comprises those compounds of Formula I where Ac is α-hydroxyphenylacetyl, thienylacetyl, α-aminophenylacetyl or trifluoromethylthioacetyl, and $R_3$ is methyl and X is oxy.

Other representative 7-acylamino substituents of the compounds of Formula I are listed below:

α-hydroxyphenylacetamido
α-aminophenylacetamido
α-amino-4-hydroxyphenylacetamido
trifluoromethylthioacetamido
2,2,2-trifluoroethylsulfinylacetamido
2,2,2-trifluoroethylthioacetamido
cyanoacetamido
α-carboxythienylacetamido
α-carboxyphenylacetamido
α-sulfophenylacetamido
methylsulfonylacetamido
cyanomethylthioacetamido
3-sydnoneacetamido
1-tetrazolylacetamido
2-thienylacetamido
syn-2-methoxyimino-2-α-furylacetamido
4-pyridylthioacetamido
o-aminomethylphenylacetamido.

Also covered in this invention are the pharmaceutically acceptable, nontoxic derivatives of the compounds of Formula I from which they derive utility: the salts, as stated above easily split ester or ether derivatives of either a carboxy or hydroxy function, amide derivatives such as those at an amino radical such as in a 7-phenylglycylamino group, for example the furyl, pyranyl, oxolanyl or oxiranyl-carbonylamide derivatives, the solvates such as hydrates or alcoholates. As examples of these one skilled in the art would be able to prepare and use the alkali metal salts such as the sodium or potassium salts (for example using sodium or potassium 2-ethyl hexanoate), ammonium salts, organic amine salts such as those with procaine or dibenzylethylenediamine or the easily hydrolyzed esters or Schiff base derivatives (or equivalent oxazolidines) at any amine function. Examples of such esters are benzhydryl, benzyl, p-methoxybenzyl, glycyloxymethyl, pivaloyloxymethyl, benzyloxymethyl, acetoxymethyl, trichloroethyl, t-butyl. It should be noted that when the ester or other protective or functional derivatives are prepared and/or used as intermediates either mildly alkaline or hydrogenation conditions for removal should be used because of the lability of the oxazine ring to strongly acid conditions.

Optical isomers of course are possible due to assymetric carbon atoms in the 7-acylamine. These may be separated or preferably as is known to this art, prepared by using the isomeric acylating agent. The D-isomers are most active. Also the two hydrogen atoms at positions 6 and 7 are in the cis position due to the stereospecific nature of the cyclization reaction used in preparing the starting material. Diasteroisomers are therefore possible here. These may be separated by known methods such as fractional crystallization of a brucine salt at the intermediate stage or at the final product level.

Also possible are isomers at the 2 and 4-positions of the 3-oxo-1-azabicyclo[4.2.0]octane ring. We have assumed from model studies that the biologically most active compounds are those in which the $2\beta$-carboxy configuration is in combination with a $4\alpha$ alkoxy substituent. However, all of the possible isomers are biologically active as well as potentially interconvertable by chemical means and are part of this invention. It should be specifically noted that the most active isomers possess the opposite $C_4$ configuration to the natural penicillins and $\Delta^2$ cephalosporins. To date we have not carried out X-ray studies of the isomeric forms isolated to confirm our assumptions.

The compounds of Formula I have demonstrable antibacterial activity against Gram-positive and especially Gram-negative organisms. Minimum inhibitory concentrations (MIC's) range from 6.3 to 400 µg/ml in in vitro testing. Test results for the compound cis-7-phenoxyacetamido-4α-methoxy-8-oxo-3-oxa-1-azabicyclo[4.2.0]octane-2β-carboxylic acid (A) and cis-7-(2-D-formyloxy-2-phenylacetamido)-4-α-methoxy-8-oxo-3-oxa-1-azabicyclo[4.2.0]octane-2β-carboxylic acid (B) are given below:

| Bacteria | MIC (µg/ml) | | | |
|---|---|---|---|---|
| | A | B | Cefazolin | |
| S. aureus HH 127 | 100 | 50 | 0.4, | 0.4 |
| S. aureus SK 23390 | 50 | 50 | 0.2, | 0.2 |
| S. villaluz SK 70390 | >200 | >200 | 100, | 100 |
| Strep. faecalis HH 34358 | >200 | >200 | 3.1, | 6.3 |
| E. coli SK 12140 | 100 | 6.3 | 3.1, | 1.6 |
| E. coli HH 33779 | 100 | 6.3 | 0.8, | 1.6 |
| Kleb. pneumo. SK 4200 | 100 | 6.3 | 0.8, | 1.6 |
| Kleb. pneumo. SK 1200 | 50 | 12.5 | 0.4, | 0.8 |
| Salmonella ATCC 12176 | 50 | 3.1 | 0.4, | 0.8 |
| Pseudo. aerug. HH 63 | >200 | >200 | >200, | >200 |
| Serrati marc. ATCC 13880 | >200 | 25 | 100, | 200 |
| Proteus morgani 179 | >200 | 25 | 100, | 100 |
| Entero aerog. ATCC 13048 | 200 | 125 | 0.8, | 1.6 |
| Entero. cloacae HH 31254 | 200 | 6.3 | 0.8, | 0.8 |
| Proteus mirabilis 444 | 100 | 125 | 3.1, | 3.1 |

From these data the activity of Compound 3 is particularly high against Serratia and *Proteus morgani*. The isomer of Compound A with a 2α-carboxy group as the sodium salt had much less activity than the 2β-isomer but still had weak activity against Staph. aureus (400). Thus the compounds of Formula I have antibacterial activity. They also have utility in the laboratory as sterilizing agents. The more active isomers and their derivatives can be used as antibacterial agents for treating infected subjects.

Pharmaceutical compositions having antibacterial activity which comprise a pharmaceutical carrier containing an active but non-toxic quantity of a compound of Formula I as well as methods of combatting bacterial infections by administering such a composition to an infected host in a non-toxic amount sufficient to combat such infections are also objects of this invention. The administration may be orally or by parenteral injection such as subcutaneously, intramuscularly or intravenously. The injection of suitably prepared sterile solutions or suspensions containing an effective, non-toxic amount of the new cephalosporix compound is a preferred route of administration.

The compounds of Formula I are formulated and administered in the same manner as other cephalosporin or penicillin derivatives. The dosage regimen comprises administration, preferably by injection, of an active but non-toxic quantity of a compound of Formula I selected from the dosage unit range of about 500 mg. to 1.5 g. with the total daily dosage regimen being from about 1-6 g. The precise dosages are dependent upon the age and weight of the subject and on the infection being treated and can be determined by those skilled in the art based on the data disclosed herein compared with that available to the art attained with known cephalosporins. Comparison of the MIC spectrum with that of cefazolin above also helps determine the effective dose.

The compounds of this invention are prepared by the unique synthetic pathway outlined as Scheme A.

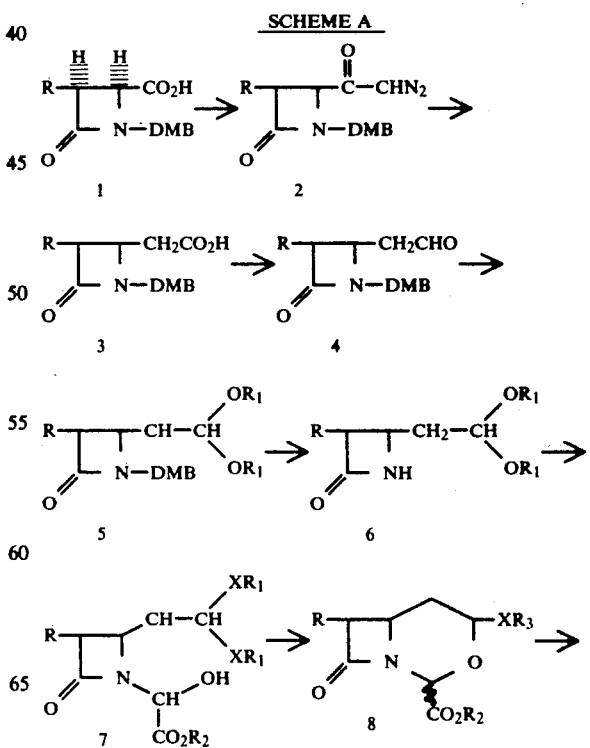

SCHEME A

-continued
SCHEME A

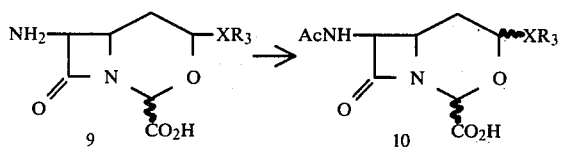

In this series of reactions, R represents a blocked or protected amino function which can be deblocked or otherwise converted to amino under conditions which will not split either the lactam (base) or oxazine (acid) rings. Exemplary are azido, carbobenzoxy, phthalimido, succinimido, maleimido or 4,5-diphenyl-2-oxo-4-oxazolin-3-yl. DMB represents 2,4-dimethoxybenzyl, 4-methoxybenzyl, trityl, benzhydryl, methoxy substituted benzhydryl and the like. $R_1$ represents allyl, methallyl, lower alkyl of from 1-4 carbon atoms which may be optionally substituted by phenyl or halo such as fluoro, chloro or bromo or, when taken together, ethylene or trimethylene. $R_2$ represents a carboxylic blocking agent removable under non-acidic, lactam sparing conditions such as benzhydryl, trityl, benzyl or p-methoxybenzyl, $R_3$ is as defined above and represents a lower alkyl, allyl, methallyl, halo lower alkyl, benzyl or hydroxy lower alkyl and Ac together with X are as defined in Formula I, said lower alkyl group having most conveniently from 1-4 carbon atoms.

Most useful are the compounds in which R is azido, DMB is 2,4-dimethoxybenzyl or its equivalent, $R_1$ is methyl or ethyl, $R_2$ is benzhydryl, $R_3$ is methyl or ethyl; X is oxy and Ac is as defined above.

The synthesis of Scheme A has a number of significant features. With a tertiary blocked amino group at 3 and the 1-nitrogen blocked, the 2-carboxylic acid is built up to an acetaldehyde function (4 and 5) having an ethylene skeleton either through a diazo or through a nitro intermediate (Scheme B).

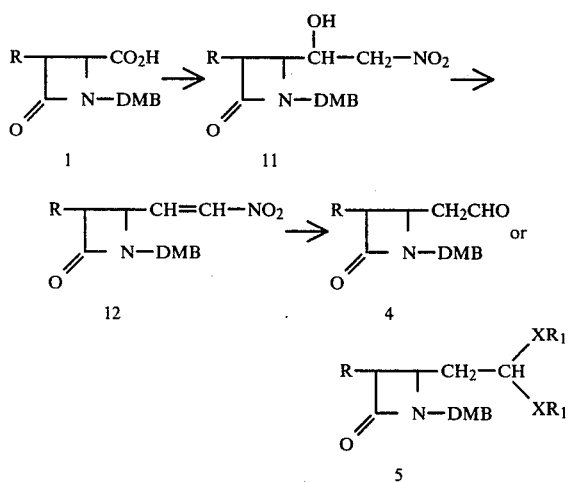

The 2-acetal intermediate (6) is reacted with a glyoxylic acid ester to form the 1-glycolic acid ester (7) which is cyclized by a condensation reaction in the presence of a catalytic source of protons such as p-toluenesulfonic acid or other acids of similar strengths. Conveniently the reaction is run in an inert organic solvent in which the glycolic acid is soluble at about room temperature for about 30 minutes to 2 hours. Suitable solvents are methylene chloride, chloroform, ethyl acetate etc. usually anhydrous. A further aspect of this reaction is adding an excess of molecular sieve pellets (4A) as an alcohol/water absorbant. Another method is dissolving the glycolic acid derivative in organic solvent such as benzene-ethyl acetate and passing the solution over a silica gel column. This reaction (7→8) is another aspect of this invention.

The 7-amino function on the new formed 3-oxo-1-aza-bicyclo[4.2.0]octane ring (8 or 9) is regenerated from 7-blocked amino by catalytic hydrogenation in the case of the 7-azido or 4,5-diphenyl-2-oxo-4-oxazolin-3-yl compounds or reaction with methylhydrazine, hydrazine sulfate, or dimethylaminopropylamine in the case of the 7-phthalimido type compounds.

The compounds of Formula I are prepared by N-acylation of intermediates whose structures have a 7-amino group represented by the structural formula IV when $R_5$ is amino.

Important intermediates of this invention are those of the following formula:

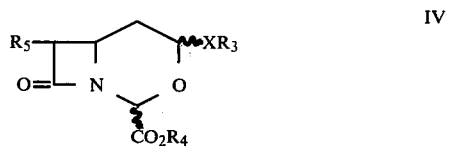

In which $R_4$ is hydrogen or $R_2$; X, $R_2$ and $R_3$ is as defined above and $R_5$ is amino or blocked amino. As noted, appropriate blocking of reactive groups such as amino or carboxyl may be present.

The acylation may employ any of the N-acylating agents known to the penicillin or cephalosporin arts containing pharmaceutically acceptable acyl groups as described hereabove with the proviso that strongly acid conditions in the acylation or subsequent removal of any amino, sulfo, carboxy or hydroxy protective groups present are not used due to the potential lability of the oxazine ring of the nucleus. The carboxylic acid of the acylating agent may be activated by any of the standard art methods such as conversion to the mixed anhydride, acid chloride, acid imidazolide or activated ester. In addition a reagent such as dicyclohexylcarbodiimide or carbonyldiimidazole can be used with the acid itself if the 2-carboxy group is protected such as by benzhydryl, trityl, p-methoxybenzyl or other groups which may be removed by catalytic hydrogenation such as palladium on charcoal in ethanol. Among the useful acylating agents are the α-azidophenylacetic acid mixed anhydrides and chlorides which may then be converted directly to the desired substituted or unsubstituted 7-glycyl derivative.

Other useful protecting groups which may be used are trimethylsilyl for hydroxyl groups, carbobenzoxy or enamine (Dane salt) for amino groups as in the glycine series. For a comprehensive review of amino, sulfo, carboxyl or hydroxy protective groups one skilled in the art may refer to "Protective Groups in Organic Chemistry", J. F. W. McOmie, Plenum Press, 1973, Chapters 2 and 3.

The following examples are intended to teach the practices of the invention described above to those skilled in the art. All temperatures are Centigrade.

EXAMPLE 1

Methyl cis-1-(2,4-Dimethoxybenzyl)-3-azido-4-oxoazetidine-2-carboxylate

Method A

To a solution of 15.1 g (0.149 mole) of amidoacetic acid in 130 ml of anhydrous methylene chloride at 0° (ice bath) was added dropwise 21.0 ml (0.15 mole) of trifluoroacetic anhydride. This mixture was stirred at 0° for 15 minutes and then 20.8 ml (0.15 mole) of triethylamine was added dropwise. Stirring was continued for an additional 43 minutes and then the entire reaction mixture was transferred under argon into an additional funnel which was cooled externally by dry ice. The addition funnel was attached to a flask containing methyl N-(2,4-dimethoxybenzyl)iminoacetate (prepared from 16.82 g of 2,4-dimethoxybenzylamine and 10.05 g of methyl glyoxalate), anhydrous methylene chloride (200 ml), and triethylamine (20.8 ml, 0.15 mole). The solution of the mixed anhydride was added dropwise from the addition funnel to the solution of imine at 0°. Stirring was continued at 0° for 1 hour and then the dark reaction mixture was transferred to a separatory funnel and washed with $H_2O$, aqueous $NaHCO_3$ and brine and then dried over anhydrous magnesium sulfate. The solvents were removed in vacuo and the residue chromatographed on 300 g of silica gel (70–230 mesh) affording an off-white solid which was further purified by trituration with ether to give 14.45 g (45%) of the title product as a white solid; tlc: benzene:ethyl acetate (1:1), silica gel GF, Rf=0.64. Recrystallization from ethyl acetate-hexane afforded an analytical sample, mp 82°–84°.

Method B

A solution of 1.6 g (9.55 mmol) dimethoxybenzylamine in 5 ml of $CH_2Cl_2$ was rapidly added at 0° to a solution of 1.06 g (10 mmol) freshly distilled methyl glyoxylate in 15 ml $CH_2Cl_2$. A slight exotherm occurred and water droplets appeared. Magnesium sulfate (5 g) was added and the mixture stirred at 0° for 2 hours. Fresh magnesium sulfate (1.0 g) was added, the magnesium sulfate removed by filtration under argon and washed with a minimum of $CH_2Cl_2$.

To a solution of 3.8 g (36 mmol) of azidoacetic acid (pumped in high vacuum 3 hr) in 125 ml of $CH_2Cl_2$ was added 10.6 ml (76 mmol) of triethylamine with cooling. Magnesium sulfate (3 gm) was added, the mixture stirred 10 minutes at room temperature, filtered under argon and washed with a 25 ml $CH_2Cl_2$.

The azidoacetic acid solution was added at 0° to the imine, sufficient methylene chloride was added to bring the total volume to 200 ml, the solution cooled to 0° under argon and 5.3 ml (30 mmol) trifluoroacetic anhydride added slowly over ½ hour with vigorous stirring and cooling. The mixture was stirred for 1 hour at 0°, allowed to warm to room temperature, transferred to a separatory funnel, washed with water, 5% $NaHCO_2$, 2% phosphoric acid and 5% $NaHCO_3$, dried over magnesium sulfate-charcoal, filtered and the filtrate was retreated twice with charcoal and evaporated to dryness. The residue was dissolved in a minimum of ether and stored at −20° to allow crystallization. The crystalline mass was isolated and washed with cold ether to give 1.9 gm (64%) product, mp 79°–80.5°.

Method C

A solution of 1.6 g. of 2,4-dimethoxybenzylamine in 15 ml. of methylene chloride was shaken with an excess of magnesium sulfate then reacted with 1.05 g of methyl glyoxylate in 2 ml of methylene chloride at 25° (room temperature) overnight. The mixture was filtered, stripped and degassed with argon.

A solution of 1.5 g of azidoacetic acid in 25 ml of methylene chloride was cooled to 0° then reacted with 1.3 ml of oxalyl chloride with 1.2 ml of pyridine in 3 ml of methylene chloride at 0°. Argon was passed through the mixture which was stirred for one hour.

The imine from above was taken into 20 ml of methylene chloride with 4.15 ml of triethylamine. The solution of azidoacetyl chloride was added dropwise at 0°. After one hour at 0° the mixture was washed with water, sodium bicarbonate solution, salt solution, dried and stripped. After passing over a silica gel column with methylene chloride the yield was 1.31 g of the desired compound.

Substitution of ethyl glyoxylate, n-butyl, tert. butyl, benzyl or methoxybenzyl glyoxylate for methyl glyoxalate gives the corresponding ester congeners of the title compound.

EXAMPLE 2

Cis-1-(2,4-dimethoxybenzyl)-2-diazacetyl-3-azido-4-azetidinone

To a suspension of 10.1 g (33 mmole) of cis-1-(2,4-dimethoxybenzyl)-3-azido-4-oxo-azetidine-2-carboxylic acid (prepared by reacting the product of example 1 with potassium carbonate in aqueous tetrahydrofuran) in 100 ml of dry benzene at 5° was added 2.54 ml (29.5 mmole) of oralyl chloride under argon. With vigorous stirring, 2.37 ml (29.5 mmole) of dry pyridine was added dropwise during which time considerable gas evolution occurred. After stirring for 1 hour, the suspension was filtered, the solid washed with cold dry benzene and the combined filtrates concentrated to one-half its volume in vacuum. The acid chloride solution was diluted to its original volume with dry benzene and added dropwise to an ethereal diazomethane solution (0.12 mole, 1.1 L) at 0° with vigorous stirring. A slow stream of argon was passed through the suspension while stirring was continued for 18 hours. 200 ml of water was added to the reaction mixture, the organic phase separated, dried ($MgSO_4$), filtered with suction, and the solvent removed by distillation at reduced pressure. The product was then triturated with 50% diethylether in hexane, collected by suction filtration, and chromatographed (silica gel: benzene with an ethyl acetate gradient up to 30%) yielding 8.5 gr (78.0%) of the title compound as light yellow crystals, mp 83°–84.5°. The corresponding α-chloroketone (2.6 gr, 22.2%) was isolated as a white crystalline solid (mp. 69°–71°).

Ethereal diazomethane was afforded by the slow addition of 30 gr of N-methyl-N'-nitro-N-nitrosoiminourea, 97% (MNNG) to a vigorously stirred solution of 51 gr of potassium hydroxide in 85 ml of water layered with 810 ml of diethyl ether at −10°. After vigorous stirring for an additional one-half hour, the either solution was carefully decanted, the aqueous phase was washed with fresh ether (3×150 ml), and the combined organic phases were dried over fresh potassium hydroxide pellets.

EXAMPLE 3

Cis-1-(2,4-dimethoxybenzyl)-3-azido-4-oxo-azetidenyl acetic acid

A solution of 6.0 gm (18.2 mmole) of cis-1-(2,4-dimethoxybenzyl)-2-diazacetyl-3-azido-4-azetidinone in 3.0 l of aqueous dioxane (50%) was degassed with argon, photolyzed using a Pyrex TM filter, and the organic solvent was removed by distillation at reduced pressure. The aqueous phase (pH=7) was then extracted with ethyl acetate (4×300 ml), adjusted to a pH of 2.5, and extracted again with ethyl acetate (4×300 ml). The last four organic extracts were combined, dried (MgSO4), treated with charcoal, filtered with suction, and solvent distilled at reduced pressure to yield 2.21 g (38%) of an off-white crystalline solid (mp. 151° d).

The neutral pH washings were combined and treated in the same fashion to yield after chromatography 2.9 g of recovered starting material and 2.6 g α-chloroketone (42%).

EXAMPLE 4

α-Cis-1-(2,4-dimethoxybenzyl)-3-azido-4-oxo-azetidenyl-acetaldehyde

To a solution of oxalyl chloride (1.37 ml, 16.2 mmol) and 5 g (15.5 mmol) of cis-1-(2,4-dimethoxybenzyl)-3-azido-4-oxo-2-azetidenyl acetic acid in 70 ml of dry glyme (freshly distilled from lithium aluminum hydride) was added dropwise over a period of 30 minutes 1.27 ml of pyridine under argon at 0°. The solution was allowed to stir at room temperature for 40 minutes after complete addition of the pyridine. The bright yellow solution was then concentrated under vacuum to half volume and quickly filtered with suction. A solution of 4.37 g (1.1 equivalents) of lithium aluminum tri-t-butoxyhydride in 100 ml of dry glyme was stirred for 30 minutes then quickly filtered through a Celite TM pad and placed in an addition funnel. The hydride solution was added dropwise under argon over a period of 2.5 hrs. to the vigorously stirred acid chloride solution at −78°. After complete addition, the reaction mixture was allowed to stir for an additional 1.5 hours. Then the dry-ice/isopropanol bath was removed and brine was added slowly, followed by addition of 3 N HCl. After dilution of the reaction mixture with ethyl acetate, the layers were separated, and the aqueous phase was extracted with ethyl acetate several times. The combined organic portions were washed with 5% sodium bicarbonate and brine, dried over magnesium sulfate and evaporated to give 4.8 g. tlc (ethyl acetate:benzene 1:1) showed one spot corresponding to aldehyde and origin material. The crude aldehyde gives satisfactory results in the next step.

EXAMPLE 5

Cis-1-(2,4-dimethoxybenzyl)-2-(2',2'-dimethoxyethyl)-3-azido-4-azetidinone

To a solution of 1.4 g (4.6 mmole) of cis-1-(2,4-dimethoxybenzyl)-3-azido-4-oxo-azetidenyl-acetaldehyde in dry benzene (10 ml) was added 4.0 ml (35.6 mmole) of freshly distilled trimethylorthoformate and 50 mg of p-toluenesulfonic acid. The mixture was stirred at 50° under an argon stream for 18 hours, diluted with 100 ml of benzene and extracted with 5% aqueous sodium bicarbonate. After drying over magnesium sulfate, the solvents were removed in vacuum and the residue chromatographed over silica gel with benzene-ethyl acetate to give 1.25 g (77%) of the title compound as a light yellow oil.

EXAMPLE 6

Cis-2-(2',2'-dimethoxyethyl)-3-azido-4-azetidinone

To a stirred solution of 1.15 g (3.28 mmole) of cis-1-(2,4-dimethoxybenzyl)-2-(2,2-dimethoxyethyl)-3-azido-4-azetidinone in 120 ml of degassed acetonitrile was added at 80°, a solution of 11.8 g (43.7 mmole) of potassium persulfate and 4.05 g (23.3 mmole) of potassium monohydrogenphosphate in 135 ml of degassed water in 6 portions over a 1 hour period. The pH of the mixture was adjusted to 6.5–7.0 with potassium monohydrogenphosphate after each addition. After one hour, the mixture was cooled to room temperature, the acetonitrile removed in vacuum and the pH adjusted to 8.0. Extraction with ethyl acetate (4×75 ml) afforded a mixture of product and 2,4-dimethoxybenzaldehyde which was chromatographed over silica gel with benzene-ethyl acetate to give 0.51 g (77%) of the title compound as a light yellow oil.

EXAMPLE 7

Diphenylmethyl cis-7-azido-4-methoxy-8-oxo-3-oxa-1-azabicyclo[4.2.0]octane-2-carboxylate To a stirred solution of 0.50 g (2.5 mmole) of cis-2-(2',2'-dimethoxyethyl)-3-azido-4-oxoazetidinone in 50 ml of dry toluene was added 0.65 g (2.7 mmole) of benzhydryl glyoxalate. The mixture was heated at 90° for 24 hours, cooled and the solvents removed in vacuum to give a mixture of diastereomeric carbinolamides.

The crude intermediate was dissolved in 30 ml of dry methylene chloride, 50 mg of p-toluenesulfonic acid and 5.0 g of 4 A molecular sieves were added and the mixture stirred at room temperature for one hour. After filtration, the mixture was diluted with methylene chloride, washed with 5% aqueous sodium bicarbonate, dried and evaporated to dryness. The resulting oil was triturated with diethyl ether to afford 160 mg (15%) of the 2β-isomer as a white crystalline material, mp 168°. nmr (CDCl3) 7.32 ppm (m,10H), 7.03 (S,1H), 5.10 (S,1H), 5.05 (dd,1H,J=3.0,2.5), 4.80 (d,1H,J=5 Hz), 4.0 (m,1H), 3.38 (s,3H), 1.9 (m,2H) ir (nujol mull) 4.72μ (N3), 5.6 (β-lactam), 5.7 (ester).

The filtrate from trituration was evaporated to dryness and chromatographed over silica gel with chloroform ethyl acetate to yield a further 11 mg (1%) of the above 2β-isomer and 300 mg (28%) of the 2α-isomer title product. NMR analysis indicates that this material is a 2:1 mixture of 4β-2α and 4α-2α isomers.

Substitution of other blocking groups as defined for R4 for the benzhydryl portion of the benzhydrylglyoxylate gives intermediates of Structure IV in which R4 may be trityl, p-methoxybenzyl, 2,4-dimethoxybenzyl, methoxy substituted benzhydryl or trityl, etc.

EXAMPLE 8

Diphenylmethyl cis-7-phenoxyacetamido-4α-methoxy-8-oxo-3-oxa-1-azabicyclo[4.2.0]octane-2β-carboxylate To a degassed solution of 133 mg (0.326 mmole) of diphenylmethyl cis-7-azido-4α-methoxy-β-oxo-3-oxa-1-azabicyclo[4.2.0]octane-2α-carboxylate in 30 ml of ethyl acetate was added 30 mg of platinum oxide and the mixture hydrogenated at atmospheric pressure for 3 hours. The catalyst was removed by filtration, the filtrate containing the important 7-amino intermediate chilled to 5° and 49 μl (0.35 mmole) of triethylamine and 49 μl (0.35 mmole) of phenoxyacetyl chloride was added slowly. The resulting suspension was stirred for 1 hour, diluted with water (20 ml), the phases separated and the organic phase washed with 5% aqueous bicarbonate, dried and evaporated to dryness. The residue was crystallized from ethyl acetate ether to give 109 mg (65%) of the title compound as a white crystalline material, mp 164.5°–166°.

Equal treatment of the isomeric material from Example 7 gives the 4α, 2αβ congener isolated as its sodium salt.

If desirable the mother liquor of the hydrogenation reaction can be evaporated and the product purified to give the appropriate blocked ester of cis-7-amino-4α-methoxy-β-oxo-3-oxa-1-azabicyclo[4.2.0]octane-2β-carboxylic acid. Intermediate IV in which $R_4$ is a carboxyl blocking group.

EXAMPLE 9

Cis-7-phenoxyacetamido-4α-methoxy-β-oxo-3-oxa-1-azabicyclo[4.2.0]octane-2β-carboxylic acid A degassed mixture of 28 mg (0.155 mmole) of diphenylmethyl cis-7-phenoxyacetamido-4α-methoxy-β-oxo-3-oxa-1-azabicyclo[4.2.0]octane-2β-carboxylate and 20 mg of 10% palladium on carbon in 25 ml of ethyl acetate was hydrogenated at atmospheric pressure for 20 minutes. The catalyst was removed by filtration and the filtrate extracted with 5% aqueous sodium bicarbonate. After separating the phases, the aqueous layer was washed with ethyl acetate, acidified to pH 2.5 and extracted with ethyl acetate. The extract was washed with brine, dried and evaporated to dryness to give 52.5 mg (88%) of product as a white crystalline solid, mp 155°–156.5°.

Substitution of trityl, p-methoxybenzyl, 2,4-dimethoxybenzyl or other acid blocking groups removable under hydrogenation conditions for the benzhydryl portion of this compound also gives the free acid product of Formula I.

EXAMPLE 10

Cis-1-(2,4-dimethoxybenzyl)-3-azido-4-oxo-2-azetidenyl formaldehyde

To a stirred solution of 16.0 g (52.3 mmol) of cis-1-(2,4-dimethoxybenzyl)-3-azido-4-oxoazetidenyl-2-carboxylic acid and 4.48 ml (52.3 mmol) of oxalyl chloride in 250 ml of glyme freshly distilled from lithium aluminum hydride was added dropwise over a period of 1 hour at 0° 4.24 ml of pyridine under argon. After stirring at room temperature for an additional one hour the reaction mixture was concentrated at reduced pressure to half volume and quickly filtered. A solution of 14.8 g of tri-t-butoxy-aluminum hydride (1.1 equivalents) in 250 ml dry glyme (prepared by stirring at room temperature overnight and filtering through Celite TM) was added dropwise under argon over 6 hours to the acid chloride solution at −78° with vigorous stirring. The reaction vessel was kept overnight at −78° then allowed to warm to room temperature after dilution with brine and 3 N hydrochloric acid. The aqueous solution was extracted several times with ethyl acetate and the combined organic extracts were extracted with 5% sodium bicarbonate several times and washed with brine. Acidification and extraction of the basic extracts with ethyl acetate gave 6.15 g of recovered starting material as a white crystalline solid. The ethyl acetate solution was dried over magnesium sulfate, filtered and concentrated to give quantitatively 9.5 g of cis-1-(2,4-dimethoxybenzyl)-3-azido-4-oxoazetidenyl-2-formaldehyde as a colorless oil. The crude aldehyde gives satisfactory yields in subsequent reactions, however, chromatography on silica gel results in a large loss of material.

EXAMPLE 11

1-[Cis-1-(2,4-dimethoxybenzyl)-3-azido-4-oxoazetidenyl]-2-nitro-1-ethanol

A solution of 39 g (0.134 mol) of crude cis-2-(2,4-dimethoxybenzyl)-3-azido-4-oxozetidenyl formaldehyde, 24.5 ml (0.16 mol) of triethylamine, and 240 ml of nitromethane in 240 ml of dimethylsulfoxide was stirred at room temperature for 18 hours. The reaction mixture was diluted with water, stirred, and extracted four times with ethyl acetate. Each ethyl acetate extract was backwashed separately with water, 3 N hydrochloric acid and brine. The combined extracts were dried over magnesium sulfate, treated with charcoal and filtered. Concentration of the ethyl acetate at reduced pressure gave an oil which afforded, after chromatography on silica gel (1:1 ethylacetate/hexane), 22.93 g (49%) of 1-[cis-1-(2,4-dimethoxybenzyl)-3-azido-4-oxo-2-azetidenyl]-2-nitro-1-ethanol as a pale yellow oil.

EXAMPLE 12

1-[Cis-1-(2,4-dimethoxybenzyl)-3-azido-4-oxo-2-azetidenyl]-2-nitroethylene

A solution of 22.93 g (65.5 mmol) of 1-[cis-1-(2,4-dimethoxybenzyl)-3-azido-4-oxoazetidenyl]-2-nitroethan-1-ol and 36.4 ml of acetic anhydride in 460 ml of pyridine was stirred at room temperature for 3 hours. The pyridine was removed under high vacuum and the residue was dissolved in ethyl acetate. The ethyl acetate solution was washed four times with water, two times with 3 N hydrochloric acid, twice with 5% sodium bicarbonate solution and once with brine. After drying over magnesium sulfate and charcoal the solution was filtered and concentrated at reduced pressure to give 20.8 g (95%) of 1-[cis-1-(2,4-dimethoxybenzyl)-3-azido-4-oxo-2-azetidenyl]-2-nitroethylene as a red oil.

EXAMPLE 13

1-Cis-1-(2,4-dimethoxybenzyl)-3-azido-4-oxo-2-azetidenyl-2-nitroethane

At −10° 3.6 g (95 mmol) of sodium borohydride was added to 100 ml of methanol, swirled and then added immediately to a vigorously stirred solution of 20.8 g (62.5 mmol) of 1-cis-1-(2,4-dimethoxybenzyl)-3-azido-4-oxo-2-azetidenyl-2-nitroethylene in 500 ml of methanol also at −10°. The reaction mixture was stirred for 20 minutes followed by a second treatment of 3.6 g sodium borohydride in the same manner. After dilution of the reaction mixture with water and acidification with 3 N hydrochloric acid, the mixture was concentrated under reduced pressure to remove the methanol. The aqueous solution was extracted with ethyl acetate. The organic extracts were washed with 5% bicarbonate and brine, dried and concentrated. The yellow oil was chromatographed on silica gel by elution with 1:1 ethylacetate/hexane giving 9 g (43%) of 1-cis-1-(2,4-dimethoxybenzyl)-3-azido-4-oxo-2-azetidenyl-2-nitroethane as a yellow oil.

EXAMPLE 14

Cis-1-(2,4-dimethoxybenzyl)-2-(2',2'-dimethoxyethyl)-3-azido-4-oxoazetidine

A solution of 9.0 g (0.027 mole) of cis-1-(2,4-dimethoxybenzyl)-3-azido-4-oxo-2-azetidenyl-2-nitroethane in 250 ml of a 0.12 molar sodium methoxide solution (700 mg sodium in 250 ml of freshly distilled methanol) was added at $-10°$ under argon to a mixture of 98 ml of conc. sulfuric acid in 260 ml of methanol at a rate of 1 drop per second. The mixture was stirred for 5 minutes, diluted with 2 L of methylene chloride and washed with a sodium phosphate solution until the wash was alkaline. The methylene chloride extract was dried over magnesium sulfate and evaporated to dryness in vacuum to give 9.4 g (100%) of the acetal as a viscous golden oil.

EXAMPLE 15

Use of the 3-Phthalimido Blocking Group 2,4-Dimethoxybenzylamine (5.01 g, 0.03 mol) and benzyl glyoxalate (0.036 mol) were condensed as in Example 1 at 0°-5° for 2 hours. The resulting imine was dissolved in methylene chloride (800 ml) and cooled in an ice bath. Triethylamine (5.4 ml) was added followed by the dropwise addition of a solution of N-phthalimidoacetic acid chloride (7.54 g, 0.0338 mol) [*J. Amer. Chem. Soc.*, 71, 1856 (1949)] in methylene chloride (80 ml). After the reaction was stirred 2 hours, the solution concentrated and then washed with water, dilute hydrochloric acid, and dilute bicarbonate. The dried organic phase was evaporated to give benzyl cis-1-(2,4-dimethoxybenzyl)-3-phthalimido-4-oxazetidine-2-carboxylate which can be optionally purified over silica gel in 10% ethyl acetate/chloroform.

The benzyl ester in methanol was hydrogenated at 5 p.s.i. using 10% palladium on charcoal. After reaction the catalyst was removed and the desired free acid isolated by evaporation in vacuo, m.p. 198°-199.5°.

The acid is converted to cis-1-(2,4-dimethoxybenzyl)-2-(2',2'-dimethoxyethyl)-3-phthalimido-4-oxoazetidine via the nitro route of Examples 10–14 with variations of reaction conditions which would be obvious to the skilled synthetic organic chemist. The acetal is debenzylated as in Example 6 to give cis-2-(2',2'-dimethoxyethyl)-3-phthalimido-4-oxoazetidine which is condensed with benzhydryl glyoxalate and cyclized as in Example 7 and 9 to give diphenylmethyl cis-7-phthalimido-4α-methoxy-8-oxo-3-oxa-1-azabicyclo[4.2.0]octane-2β-carboxylate.

The bicyclic lactam product (8.0 g) is cooled in a dry ice-acetone bath under nitrogen then 1.1 g of methylhydrazine added. After stirring for 20 minutes the mixture is re-cooled to $-78°$ and 4.5 ml of the hydrazine added. The volatiles are removed at the pump to give 8.3 g of half opened hydrazide intermediate. This compound (3.5 g) in 50 ml of chloroform is heated on the steam bath for 30 minutes then allowed to stand several days. The liquid is evaporated to give a product of mostly cis-7-amino ester which may be optionally purified over a silica gel column using chloroform isopropanol.

The ester (1 g) is dissolved in ethanol and hydrogenated using palladium on charcoal catalyst at low hydrogen pressure. The reaction mixture is then filtered and the filtrate evaporated in vacuo to give impure cis-7-amino-4α-methoxy-8-oxo-3-oxa-1-aza-bicyclo[4.2.0]-octane-2β-carboxylic acid.

EXAMPLE 16

Use of the 3-(4,5-Diphenyl-2-oxo-4-oxazolin-3-yl Blocking Group

To a mixture containing 16.82 g (0.101 mole) of 2,4-dimethoxybenzylamine and anhydrous magnesium sulfate in 150 ml of methylene chloride at 25° is added a solution of 10.05 g (0.114 mole) of benzyl glyoxalate in 20 ml of methylene chloride. The reaction mixture is stirred at room temperature overnight (15 hours) and then is filtered and the solvents are removed in vacuo to afford the imine as a dark orange gum.

A mixture of 4,5-diphenyl-2-oxo-4-oxazolin-3-ylacetic acid (2.1 g, 7.1 mmol) [*J. Org. Chem.*, 38, 3034 (1973)], thionyl chloride (5 ml) and methylene chloride (20 ml) is refluxed for 2.5 hours. After cooling to room temperature the solvent is removed in vacuo and resulting oil crystallizes on standing. The product is triturated with etherhexane to give 4,5-diphenyl-2-oxo-4-oxazolin-3-ylacetic acid chloride; 2.0 g mp 104°-12°.

The imine (1.43 g) is dissolved in dry methylene chloride (13 ml) and triethylamine (1 ml) and cooled in an ice bath. The acid chloride (2.0 g, 6.4 mmol) in methylene chloride (10 ml) is added over a 10-minute period. After one hour, the mixture is washed with water and 5% bicarbonate, the dried solution is evaporated to a red oil which is chromatographed on 60 g of silica gel with 5% ethyl acetate in chloroform as eluant to give benzyl cis-1-(2,4-dimethoxybenzyl)-3-(4,5-diphenyl-2-oxo-4-oxazolin-3-yl)-4-oxoazetidine-2-carboxylate.

This product is converted to the acetal, which is dibenzylated, condensed with a glyoxalate ester and cyclized to give benzhydryl cis-7-(4,5-diphenyl-2-oxo-4-oxazolin-3-yl)-4α-methoxy-8-oxo-3-oxa-1-azabicyclo[4.2.0]-octane-2β-carboxylate.

A solution of the 7-blocked amino ester (2.0 g, 3.9 mmol) in 50 ml ethanol is added to 10% palladium on carbon (0.5 g). The mixture is hydrogenated for 12 hours at 50 psi and 40°. After filtration, the solvent is removed and the oil is dissolved in methylene chloride which is then washed with NaHCO$_3$ and brine and dried. The solution is evaporated to give cis-7-amino-4α-methoxy-3-oxo-1-3-oxa-1-azabicyclo-[4.2.0]octane-2β-carboxylic acid.

EXAMPLE 17

Cis-7-(2-D-formyloxy-2-phenylacetamido)-4α-methoxy-8-oxo-3-oxa-1-azabicyclo[4.2.0]octan-2β-carboxylic acid A solution of 40.8 mg (0.01 mmole) of cis-7-azido-4α-methoxy-8-oxo-3-oxa-1-azabicyclo[4.2.0]octan-2-β-carboxylic acid, benzhydryl ester (from Example 7) in 25 ml of ethyl acetate was hydrogenated at atmospheric pressure in the presence of 5 mg of platinum oxide. After 3 hours, the solution was degassed, filtered and concentrated to 15 ml. At 0°, 19 mg of D-2-formyloxyphenylacetic acid and 23 mg of dicyclohexylcarbodiimide were added and the mixture stirred for one hour at 0°. The urea was removed by filtration and the filtrate chromatographed over silica gel with chlorofom-ethyl acetate to yield 49.7 mg (92%) of amide as the benzhydryl ester in the form of a viscous oil. The amide was dissolved in 25 ml of ethyl acetate and hydrogenated for 3 hours at atmospheric pressure with 5 mg of 10% palladium on carbon. The mixture was filtered, evaporated to dryness and titurated with methylene chloridehexane to give 16.8 mg (54%) of the desired product as white crystals, mp 126°–136°.

EXAMPLE 18

Cis-7-amino-4α-methoxy-8-oxo-3-oxa-1-azabicyclo[4.2.0]octane-2β-carboxylic acid

A mixture of 95 mg (0.023 mm) of cis-7-azido-4α-methoxy-8-oxo-3-oxa-1-azabicyclo[4.2.0]octane-2β-carboxylic acid, benzhydryl ester and 25 mg of 10% palladium on carbon in 10 ml of ethanol was hydrogenated at room temperature and atmospheric pressure for 2 hours. Removal of the catalyst, evaporation of the solvents and tituration with ether affords the title compound.

EXAMPLE 19

Cis-7-(2-thienylacetamido)-4α-methoxy-8-oxo-3-oxa-1-azabicyclo[4.2.0]-octane-2β-carboxylic acid A mixture of cis-7-amino-4α-methoxy-8-oxo-3-oxa-1-azabicyclo-[4.2.0]octane-2β-carboxylic acid (from hydrogenation of 30 mg of azide) and 35 μl of triethylamine in 20 ml of cold isopropanol was treated with 30 μl of thienylacetyl chloride. After stirring at 0° for 3 hours, the mixture was filtered, the solvents removed in vacuum, the residue dissolved in ethyl acetate and extracted with 5% aqueous sodium bicarbonate. The aqueous solution was acidified with phosphoric acid and extracted with ethyl acetate, washed with brine, dried and evaporated to dryness. Tituration with ether-hexane gave 4.9 mg (20%) of the desired compound as a tan solid.

EXAMPLE 20

Using the method of Example 17 with:
2,2,2-trifluoroethylthioacetic acid gives:
  cis-7-(2′,2′,2′-trifluoroethylthioacetamido)-4α-methoxy-3-oxo-1-azabicyclo[4.2.0]octan-8-2β-carboxylic acid.
D-α-azidophenylacetic acid gives:
  D-cis-7-(2-aminophenylacetamido)-4α-methoxy-3-oxo-1-azabicyclo[4.2.0]octan-8-one-2β-carboxylic acid.
D-α-azido-p-hydroxyphenylacetic acid gives:
  D-cis-7-(α-amino-o-hydroxyphenylacetamido)-4α-methoxy-3-oxo-1-azabicyclo[4.2.0]octan-8-one-2β-carboxylic acid.
D-mandelic acid gives:
  D-cis-7-(α-hydroxyphenylacetamido)-4α-methoxy-3-oxo-1-azabicyclo[4.2.0]octan-8-one-2β-carboxylic acid.
4-pyridylthioacetic acid gives:
  cis-7-(4-pyridylthioacetamido)-4α-methoxy-3-oxo-1-azabicyclo-[4.2.0]octan-8-one-2β-carboxylic acid.

EXAMPLE 21

Using the method of Example 8 and 9 with:
trifluoromethylthioacetyl chloride gives:
  cis-7-trifluoromethylthioacetamido)-4α-methoxy-3-oxo-1-azabicyclo[4.2.0]octan-8-one-2β-carboxylic acid.
o-nitromethylphenylacetyl chloride gives:
  cis-7-(o-aminomethylphenylacetamido)-4α-methoxy-3-oxo-1-azabicyclo[4.2.0]octan-8-one-2β-carboxylic acid.

EXAMPLE 22

Using the method of Example 19 with:
cyanoacetyl pivalylanhydride gives;
  cis-7-cyanoacetamido-4α-methoxy-3-oxo-1-azabicyclo[4.2.0]-octan-8-one-2β-carboxylic acid.
1-tetrazolylacetyl chloride gives;
  cis-7-(1′-tetrazolylacetamido)-4α-methoxy-3-oxo-1-azabicyclo-[4.2.0]octan-8-one-2β-carboxylic acid.
syn-2-methoxyimino-2-furylacetyl chloride gives;
  cis-7-(syn-2-methoxyimino-2α-furylacetamido)-4α-methoxy-3-oxo-1-azabicyclo[4.2.0]octan-8-one-2β-carboxylic acid.
3-sydnoneacetic acid mixed anhydride gives:
  cis-7-(3-sydnoneacetamido)-4α-methoxy-3-oxo-1-azabicyclo-[4.2.0]-octan-8-one-2β-carboxylic acid.

EXAMPLE 23

The organic salts are prepared by reacting 100 mg. of an acid of this invention in ethyl acetate with a slight excess of the organic amine such as procaine in ether.

The alkali metal salts are prepared by reacting suchan acid in ethyl acetate with ethanolic sodium or potassium exthoxide. Alternatively the acid (for example 200 mg of the product of Examples 17 or 19) in ethyl acetate is mixed with an excess of a sodium-2-ethylhexanoate salt. Ether is gradually added to separate the salt.

EXAMPLE 24

An injectable pharmaceutical composition is prepared by dissolving 150 mg of the potassium salt of Examples 9, 17 or 19 in sterile saline solution (2.5 ml). The composition is injected parenterally into a subject infected with a susceptible bacteria from 3–5 times daily.

EXAMPLE 25

Cis-3-azido-4-oxo-2-azetidineacetaldehyde

A mixture of 500 mg (2.5 mmole) of cis-3-azido-2-(2,2-dimethoxyethyl)-4-oxoazetidine in 10 ml of 5% HCl and 10 ml of dioxane was stirred at 35° for ½ hour. The mixture was diluted with water and extracted with 50 ml of benzene. The aqueous phase was saturated with brine and extracted 10 times with 50 ml of ethyl acetate. The ethyl acetate extract was dried over magnesium sulfate and evaporated to dryness. The residue was titurated with ether to give the desired aldehyde, 235 mg (60%), mp 73°–78°.

EXAMPLE 26

Cis-3-azido-2-[2,2-di(benzylthio)ethyl]-4-oxoazetidine

A solution containing 230 mg (1.45 mmole) of cis-3-azido-4-oxo-2-azetidineacetaldehyde, 20 mg of p-toluenesulfonic acid and 0.5 ml of benzylthiol in 25 ml of benzene and 5 ml of dimethylformamide was heated under reflux for 1 hour. After cooling, the mixture was shaken with ethyl acetate and 5% sodium bicarbonate, the organic phase washed with brine, dried and evaporated to dryness. Chromatography over silica gel with chloroform afforded 83 mg (13%) of the title compound.

Using this basic reaction a wide range of alcohols or mercaptans can be reacted with the aldehyde product of Examples 25 to give the desired acetal or thioacetal which then may be submitted to the reaction described in Scheme 1 and the foregoing examples to give a wide variation of 4-substituents.

Exemplary alcohols or mercaptans to be used in this reaction are ethyl mercaptan, isopropyl alcohol, allyl alcohol or mercaptan, methallyl alcohol or mercaptan, trifluoroethanol, dichloroethanol, butyl mercaptan or ethyleneglycol (to give the 4-$\beta$-hydroxyethoxy). If the thio atoms cause trouble during the hydrogenation step the carboxy protective groups such as the methyl, ethyl, trichloroethyl or benzyl esters may be removed by mild alkaline hydrolysis such as with sodium or potassium bicarbonate or carbonate.

EXAMPLE 27

Diphenylmethyl cis-[3-azido-2-(2,2-dimethoxyethyl)-4-oxoazetidinyl]-1-hydroxyacetate A mixture of 3.0 g (15 mmole) of cis-3-azido-2-(2,2-dimethoxyethyl)-4-oxoacetidine and 5.4 g (22.5 mmole) of diphenylmethyl glyoxylate in 200 ml of toluene was heated at 90° overnight. After cooling, the toluene was removed in vacuum and the residue chromatographed on silica gel with 7:3 chloroform-ethyl acetate to afford 2.3 g of the title compound as a viscous oil. A second fraction was also obtained which was a mixture of diphenylmethyl glyoxylate and a diastereomeric isomer of the title compound.

EXAMPLE 28

Diphenylmethyl cis-7-azido-4$\alpha$-methoxy-8-oxo-3-oxa-1-azabicyclo[4.2.0]octane-2$\beta$-carboxylate A solution containing 2.0 g (4.5 mmole) of diphenylmethyl cis-[3-azido-2-(2,2-dimethoxyethyl)-4-oxoazetidinyl]-1-hydroxyacetate and 100 mg (0.5 mmole) of toluenesulfonic acid in 100 ml of methylene chloride was stirred over 10 gm of 4 Å molecular sieves for 2 hours. The mixture was filtered and the filtrate was washed with a 5% aqueous sodium bicarbonate solution, dried and evaporated to dryness. Tituration with ether afforded 1.2 gm of the title compound.

The ether solution was diluted slowly with hexane and allowed to stand for 24 hours. The crystalline material which separated was collected and recrystallized from chloroform-hexane to afford 45 mg of diphenylmethyl cis-[3-azido-2-formylmethyl-4-oxoazetidinyl]-1-hydroxyacetate, mp 135°–136°. This intermediate is used to form acetals or thioacetals as described in Example 26 which are then cyclized as described above.

EXAMPLE 29

Diphenylmethyl cis-7-azido-4$\beta$-methoxy-8-oxo-3-oxa-1-azabicyclo[4.2.0]octane-2$\beta$-carboxylate A solution containing 100 mg (0.22 mmole) of diphenylmethyl cis-[3-azido-2-(2,2-dimethoxyethyl)-4-oxoazetidinyl]-1-hydroxyacetate and 20 mg (0.1 mmole) of toluenesulfonic acid in 10 ml of methylene chloride was stirred over 5 gm of 4 Å molecular sieves for five hours. The mixture was filtered and the filtrate was washed with sodium bicarbonate, dried and evaporated to dryness. The residue was chromatographed on silica gel with chloroform as eluant. The first product eluted was the title compound, mp 170°–171°. Further elution with 95:5 chloroform-methyl acetate afforded the 4$\alpha$-2$\beta$ isomer.

EXAMPLE 30

7-D-(2-Amino-2-phenylacetamido)-4$\alpha$-methoxy-8-oxo-3-oxa-1-azabicyclo[4.2.0]octane-2$\beta$-carboxylic acid A solution of 7-azido-4-methoxy-8-oxo-3-oxa-1-azabicyclo[4.2.0]octane-2-carboxylic acid, benzhydryl ester (100 mg, 0.245 mmole) in 15 ml of ethyl acetate was hydrogenated over 20 mg of platinum oxide at atmospheric pressure for 2 hours. The catalyst was filtered and the filtrate evaporated to dryness. The residue was redissolved in 10 ml of methylene chloride, 2-azido-2-phenylacetic acid (43 mg, 0.24 mmole) and dicyclohexylcarbodiimide (50 mg, 0.25 mmole) were added at 0° and the mixture stirred for 2 hours. The mixture was filtered, the filtrate evaporated to dryness, shaken with dil. HCl and ethyl acetate, the organic phase washed with bicarbonate, brine, dried and evaporated to dryness.

The residue was chromatographed over silica gel with 4:1 benzene-ethyl acetate to give 112 mg (85%) of the product as a white solid.

A solution of 7-(2-azido-2-phenylacetamido)-4$\alpha$-methoxy-8-oxo-3-oxa-1-azabicyclo[4.2.0]octane-2$\beta$-carboxylic acid, benzhydryl ester (83 mg, 0.15 mmole) in 50 ml of methanol was hydrogenated over 10 mg of 10% palladium on carbon at atmospheric pressure for 4 hours, replacing the catalyst after 2 hours. After filtering the catalyst, the filtrate was concentrated to dryness, dissolved in 5 ml of methanol and the product precipitated with ether to afford 43 mg (83%) of a tan solid, m.p. 184°–188°.

EXAMPLE 31

Cis-7-(2-carboxy-2-phenylacetamido)-4$\alpha$-methoxy-8-oxo-3-oxa-1-azabicyclo[4.2.0]octane-2$\beta$-carboxylic acid monocyclohexylamine salt pentahydrate A solution of diphenylmethyl-cis-7-azido-4$\alpha$-methoxy-8-oxo-3-oxa-1-azabicyclo[4.2.0]octane-2$\beta$-carboxylate (250 mg, 0.6 mmole) in ethylacetate (100 ml) was hydrogenated at 30 psi over platinum oxide (50 mg) for 3 hours. After filtration of the catalyst the filtrate containing the 7-amino intermediate was concentrated in vacuo to a volume of 60 ml. The solution was cooled to 5° and treated with triethylamine (85 μl, 0.61 mmole) followed by dropwise addition of benzyl-2-chlorocarbonyl-2-phenylacetate (176 mg, 0.61 mmole) in ethylacetate (10 ml). The reaction mixture was allowed to warm to room temperature and after stirring for three hours was washed with 5% bicarbonate, brine, dried and concentrated to leave an orange oil. Chromatography on silica gel with chloroform as the eluting solvent afforded the product (167 mg, 44%) as a white solid, m.p. 67°–71° (diphenylmethyl-cis-7-(2-benzylcarboxylate-2-phenylacetamido)-4$\alpha$-methoxy-8-oxo-3-oxa-1-azabicyclo[4.2.0]-octane-2$\beta$-carboxylate).

A solution of cis-7-2-benzylcarboxylate-2-phenylacetamido)-4$\alpha$-methoxy-8-oxo-3-oxa-1-azabicyclo[4.2.0]octane-2$\beta$-carboxylic acid benzhydryl ester (97.6 mg, 0.15 mmole) in ethylacetate (25 ml) containing cyclohexylamine (332 μl, 3.7 mmole, ca. 2.5 eq.) was hydrogenated at 1 atm. over 10% palladium on carbon for 1.5 hours. After filtration of the catalyst the filtrate was washed with water (4×2 ml) and the aqueous washes lyophilized to give the title product as a white, hydroscopic solid 24.3 mg (28.5%).

$C_{23}H_3N_3O_8 \cdot 5H_2O$; Calculated: C, 48.67; H, 7.29; N, 7.40. Found: C, 49.28; H, 7.16; N, 7.06.

What is claimed is:

1. The method of preparing a compound of the formula:

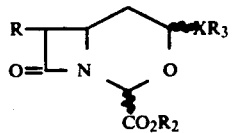

in which R is a blocked amino, X is thio or oxy, $R_2$ is a carboxyl blocking group and $R_3$ is lower alkyl comprising reacting in an inert solvent at about room temperature with a catalytic source of protons a compound of the formula:

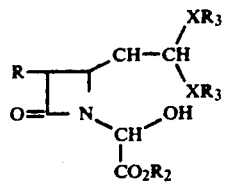

in which R, $R_2$, X and $R_3$ are as defined above.

2. The process of claim 1 in which R is azido, X is oxy, $R_1$ is methyl or ethyl, $R_2$ is benzhydryl and the source of protons is p-toluenesulfonic acid.

* * * * *